(12) United States Patent
Harandi et al.

(10) Patent No.: US 11,603,340 B2
(45) Date of Patent: Mar. 14, 2023

(54) METHODS FOR METHANOL-TO-GASOLINE CONVERSION WITH POST-PROCESSING OF HEAVY GASOLINE HYDROCARBONS

(71) Applicant: ExxonMobil Technology and Engineering Company, Annandale, NJ (US)

(72) Inventors: Mohsen N. Harandi, New Hope, PA (US); Mitch L. Hindman, Hamilton, VA (US); Suriyanarayanan Rajagopalan, Spring, TX (US)

(73) Assignee: EXXONMOBIL TECHNOLOGY AND ENGINEERING COMPANY, Annandale, NJ (US)

(*) Notice: Subject to any disclaimer, the term of this patent is extended or adjusted under 35 U.S.C. 154(b) by 80 days.

(21) Appl. No.: 17/014,991

(22) Filed: Sep. 8, 2020

(65) Prior Publication Data
US 2021/0078921 A1  Mar. 18, 2021

Related U.S. Application Data

(60) Provisional application No. 62/901,470, filed on Sep. 17, 2019.

(51) Int. Cl.
*C07C 5/22* (2006.01)
*C07C 41/09* (2006.01)
(Continued)

(52) U.S. Cl.
CPC ............ *C07C 5/2206* (2013.01); *C07C 41/09* (2013.01); *C10G 3/49* (2013.01); *C10L 1/023* (2013.01);
(Continued)

(58) Field of Classification Search
CPC .. C10L 1/023; C10L 1/026; C10L 3/12; C10L 2200/0423; C10L 2200/0446;
(Continued)

(56) References Cited

U.S. PATENT DOCUMENTS 4,665,249 A   5/1987   Mao et al.
9,938,205 B2  4/2018   Du et al.
(Continued)

*Primary Examiner* — Latosha Hines
(74) *Attorney, Agent, or Firm* — Shook, Hardy & Bacon L.L.P.

(57) ABSTRACT

Methanol-to-gasoline conversion may be performed using a heavy gasoline treatment, followed by a separation operation. Methanol may be converted into a first product mixture comprising dimethyl ether (DME) under DME formation conditions. In a methanol-to-gasoline (MTG) reactor, the first product mixture may be converted under MTG conversion conditions to produce a second product mixture comprising light gasoline hydrocarbons and untreated heavy gasoline hydrocarbons. The untreated heavy gasoline hydrocarbons may be separated from the light gasoline hydrocarbons and transferred to a heavy gasoline treatment (HGT) reactor. The untreated heavy gasoline hydrocarbons may be catalytically reacted in the HGT reactor to form a third product mixture. A heavy hydrocarbon fraction may be separated from the third product mixture. The heavy hydrocarbon fraction includes heavy gasoline hydrocarbons having a lower boiling endpoint than does the untreated heavy gasoline hydrocarbons.

12 Claims, 1 Drawing Sheet

(51) Int. Cl.
    *C10G 3/00*     (2006.01)
    *C10L 1/02*     (2006.01)
    *C10L 3/12*     (2006.01)

(52) U.S. Cl.
    CPC .......... *C10L 1/026* (2013.01); *C10G 2400/02* (2013.01); *C10G 2400/04* (2013.01); *C10L 3/12* (2013.01); *C10L 2200/0423* (2013.01); *C10L 2200/0446* (2013.01); *C10L 2290/24* (2013.01)

(58) Field of Classification Search
    CPC ... C10L 2290/24; C07C 5/2206; C07C 41/09; C10G 3/49; C10G 2400/02; C10G 2400/04
    See application file for complete search history.

(56) References Cited

U.S. PATENT DOCUMENTS

| | | | |
|---|---|---|---|
| 2012/0116137 A1* | 5/2012 | Fang | C10G 3/46 422/187 |
| 2015/0175898 A1 | 6/2015 | McCarthy et al. | |
| 2016/0102031 A1 | 4/2016 | Du et al. | |
| 2016/0178132 A1* | 6/2016 | Harandi | C10G 45/00 585/254 |
| 2017/0121615 A1 | 5/2017 | Harandi et al. | |
| 2017/0137342 A1 | 5/2017 | Behkish et al. | |
| 2017/0137720 A1 | 5/2017 | Harandi et al. | |
| 2018/0170823 A1 | 6/2018 | Rajagopalan et al. | |

\* cited by examiner

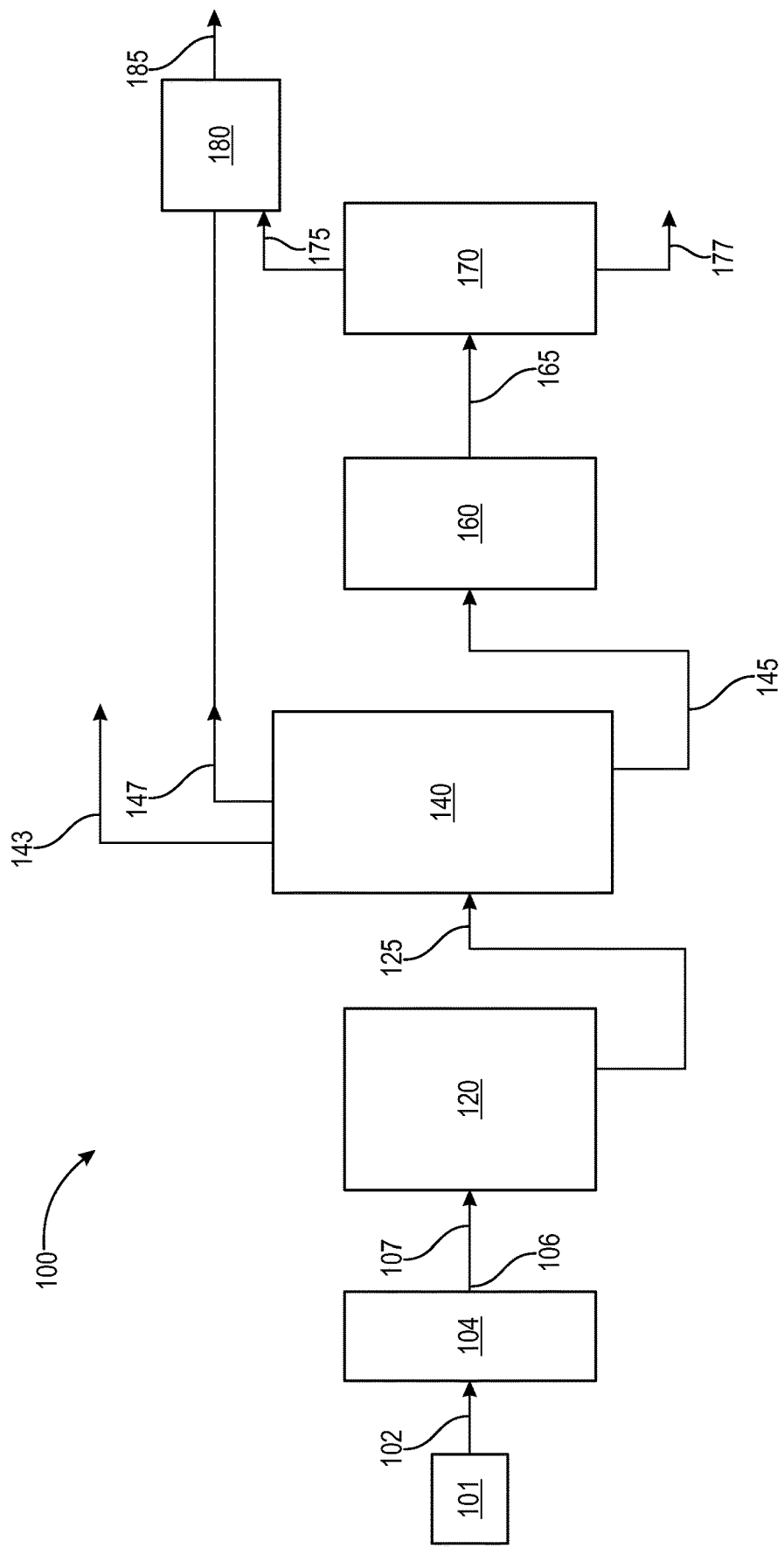

METHODS FOR METHANOL-TO-GASOLINE CONVERSION WITH POST-PROCESSING OF HEAVY GASOLINE HYDROCARBONS

CROSS REFERENCE TO RELATED APPLICATIONS

The application claims priority to U.S. Provisional Application Ser. No. 62/901,470 filed Sep. 17, 2019 which is herein incorporated by reference in its entirety.

FIELD

The present disclosure relates to methanol-to-gasoline conversion methods.

BACKGROUND

During methanol-to-gasoline (MTG) conversion processes, an equilibrium mixture of methanol and dimethyl ether (DME) is contacted with a zeolite catalyst, such as ZSM-5, in the presence of recycled light hydrocarbon gas, under conditions effective to convert the equilibrium mixture into gasoline, which may also be referred to as gasoline hydrocarbons. Typically, in such processes, a DME reactor is supplied with a methanol feed that usually comprises approximately 7 mol. % water (about 4.1 wt. %). Process guidance usually suggests a maximum water content of 5 wt. % for the methanol feed provided to the DME reactor. The DME reactor, which also includes a suitable catalyst, produces an equilibrium mixture comprising methanol, DME, and approximately 40 mol. % water (~25 wt. %), with the additional water resulting from dehydration of the methanol to form the DME.

The equilibrium mixture from the DME reactor is then fed, usually directly, to an MTG reactor (e.g., an axial-flow, packed-bed reactor, also called a fixed-bed reactor). The MTG reactor produces a mixture of heavy and light gasoline hydrocarbons and light hydrocarbon gas (liquid petroleum hydrocarbons). MTG conversion processes, due at least in part to the shape-selectivity of the ZSM-5 catalyst, also produce durene (1,2,4,5-tetramethylbenzene) as a high-melting component (174.6° F.). If present in sufficient quantities, durene can lead to undesired solidification/crystallization when the durene-laden gasoline is stored or used in cold climates.

To limit durene-induced solidification, the mixture obtained from the MTG reactor may be subjected to a series of separation processes, followed by a treatment process using a suitable catalyst or plurality of catalysts to reduce the durene content to acceptable levels (<2 wt. %) in the final product (finished) gasoline. To accomplish the foregoing, the mixture obtained from the MTG reactor may be cooled and deethanized, followed by feeding the resultant product to a stabilizer to separate other light hydrocarbons (liquid petroleum gas hydrocarbons) from gasoline hydrocarbons. The gasoline hydrocarbons obtained from the stabilizer may then be fed to a splitter to concentrate the durene in a bottoms portion, which contains heavy gasoline hydrocarbons and may referred to as "heavy gasoline." The overhead portion obtained from the splitter contains light gasoline hydrocarbons and may be referred to as "light gasoline." The concentration of durene in the heavy gasoline so obtained may approach or exceed approximately 50% by weight. Accordingly, the heavy gasoline may be subsequently treated in a heavy gasoline treatment (HGT) reactor to isomerize the durene into less problematic hydrocarbons. The durene content may be decreased to about 75-80% of its original value in this process.

A final product gasoline may be formed by blending the treated heavy gasoline having a decreased durene content with the light gasoline, usually at a blend ratio such that the durene content is about 2 wt. % or less. Although HGT processes may be effective to decrease the durene content into an acceptable range, a small amount of additional hydrocarbons having a higher number of carbon atoms may also be concurrently formed or have formed previously upstream. Such "extra heavy hydrocarbons" may lead to the boiling endpoint specification being exceeded in the final product gasoline. As a result, it may not be possible to fully or effectively utilize the heavy hydrocarbons obtained from conventional HGT processes. Certain countries, for instance, specify a boiling endpoint specification for finished gasoline that is lower than that typically achievable when blending the heavy hydrocarbons obtained from conventional MTG processes.

SUMMARY

The present disclosure provides methods for methanol-to-gasoline conversion featuring a separation operation following a heavy gasoline treatment. The methods comprise: providing a feed comprising methanol to a dimethyl ether (DME) reactor; converting at least a portion of the feed in the DME reactor under dimethyl ether formation conditions to produce a first product mixture comprising dimethyl ether; transferring the first product mixture to a methanol-to-gasoline (MTG) reactor; converting at least a portion of the first product mixture in the MTG reactor under methanol-to-gasoline conversion conditions to produce a second product mixture comprising light gasoline hydrocarbons and untreated heavy gasoline hydrocarbons; separating the untreated heavy gasoline hydrocarbons from the light gasoline hydrocarbons; transferring the untreated heavy gasoline hydrocarbons to a heavy gasoline treatment (HGT) reactor; catalytically reacting the untreated heavy gasoline hydrocarbons in the HGT reactor to form a third product mixture; and separating a heavy hydrocarbon fraction from the third product mixture, the heavy hydrocarbon fraction comprising heavy gasoline hydrocarbons having a lower boiling endpoint than do the untreated heavy gasoline hydrocarbons.

BRIEF DESCRIPTION OF THE DRAWING

The following FIGURE is included to illustrate certain aspects of the present disclosure, and should not be viewed as an exclusive embodiment. The subject matter disclosed is capable of considerable modifications, alterations, combinations, and equivalents in form and function, as will occur to one of ordinary skill in the art and having the benefit of this disclosure.

THE FIGURE shows a diagram of a system demonstrating various operations that may be performed in the course of converting methanol to gasoline according to various embodiments of the present disclosure.

DETAILED DESCRIPTION

The present disclosure relates to methanol-to-gasoline (MTG) conversion processes and, more particularly, methanol-to-gasoline conversion processes featuring post-processing of heavy gasoline hydrocarbons prior to forming final product gasoline.

During conventional methanol-to-gasoline (MTG) conversion processes, methanol is fed to a dimethyl ether (DME) reactor, which produces an equilibrium mixture of methanol, water and DME in the presence of a suitable catalyst. The equilibrium mixture, which may be referred to as a "first product mixture" herein, is then fed to a methanol-to-gasoline (MTG) reactor that converts the DME into gasoline hydrocarbons using a suitable catalyst to afford a mixture of gasoline hydrocarbons and light hydrocarbon gas. The mixture obtained from the MTG reactor may also be referred to as a "second product mixture" herein and may also include durene (1,2,4,5-tetramethylbenzene). The gasoline hydrocarbons may represent any combination of light gasoline hydrocarbons and heavy gasoline hydrocarbons.

The second product mixture obtained from the MTG reactor may be subjected to a series of separation or stabilization processes, followed by a treatment process employing a suitable catalyst to decrease the durene content to an acceptable level (about 2 wt. % or less) in the final product gasoline. As an example, the second product mixture obtained from the MTG reactor may be cooled and sent to a de-ethanizer to remove ethane, and the resultant product stream may be fed to a stabilizer to separate light hydrocarbon gas from the gasoline hydrocarbons. A portion of the light hydrocarbon gas may be recycled to the MTG reactor, which may aid in regulating the temperature therein. The gasoline hydrocarbons from the stabilizer are then fed to a splitter to concentrate the durene in another heavy portion, which may be referred to as "untreated heavy gasoline hydrocarbons" herein and may comprise up to about 10% of the feed to the splitter, as an example. The other fraction obtained from the splitter may be referred to herein as "light gasoline hydrocarbons." The durene in the untreated heavy gasoline hydrocarbons may constitute about 99-99.9 wt. % of the total durene formed in the MTG reactor, and the concentration of durene in the untreated heavy gasoline fraction may approach or exceed, for example, about 50% by weight. The heavy gasoline hydrocarbons may then be treated in a heavy gasoline treatment (HGT) reactor to decrease the durene content in the presence of a suitable catalyst for isomerizing the durene into less problematic products. The HGT reactor may include a plurality of catalysts for this purpose. The durene content in the treated heavy gasoline hydrocarbons, which may be referred to as a "third product mixture" herein, may be decreased by approximately 60-90% of its original value, as an example. In some process implementations, the durene content in the treated heavy gasoline hydrocarbons may be decreased by approximately 70-80% of its original value. Undesirably, a small amount of heavier hydrocarbons that may affect the boiling endpoint of the final product gasoline may concurrently form during the HGT process. Heavier hydrocarbons may also form at earlier points upstream during the methanol-to-gasoline conversion process as well.

The MTG conversion processes disclosed herein further include an additional fractionation section downstream of the HGT reactor, in contrast to conventional MTG conversion processes. After being discharged from the HGT reactor, the third product mixture containing treated heavy gasoline hydrocarbons is provided to another separation unit, which may be referred to as a "heavy gasoline splitter" (HGS). The heavy gasoline splitter separates or removes an "extra heavy hydrocarbon fraction" from the remaining heavy gasoline hydrocarbons. Residual durene may also be removed with the extra heavy hydrocarbon fraction in this process. Following separation, the remaining heavy gasoline hydrocarbons no longer contain significant durene or extra heavy hydrocarbons, thereby allowing the heavy hydrocarbon fraction to be more effectively used. In addition to durene, the extra heavy hydrocarbon fraction may contain a majority or all components having a boiling point in the range of about 325° C. to about 427° C. or more, which may be considered a light diesel hydrocarbon fraction. Components that may be present in the extra heavy hydrocarbon fraction include, for example, kerosene, aromatics solvent, and low pour diesel blend components. For example, the heavy gasoline splitter may provide about 5-20 wt. % light diesel hydrocarbons relative to the weight of the third product mixture received from the HGT reactor. The present disclosure allows such light diesel hydrocarbons to be more effectively used as well. As a non-limiting example, the light diesel hydrocarbons, with or without further processing, may be blended (e.g., combined and mixed) with another diesel source (regular diesel or biodiesel) from other parts of a refinery or elsewhere to form a diesel blend having desired properties.

Removing light diesel hydrocarbons and other extra heavy hydrocarbons from the treated heavy gasoline hydrocarbons in the third product mixture may reduce or eliminate concerns about meeting boiling endpoint specification requirements in a final product gasoline. The heavy hydrocarbon fraction obtained from the third product mixture, but not light diesel hydrocarbons or other extra heavy hydrocarbons, may be blended with the light gasoline hydrocarbons formed earlier in the MTG process to afford a final product gasoline having both a decreased durene content and a lower boiling endpoint specification than that otherwise attainable without the additional product splitting described above. As mentioned previously, the light diesel hydrocarbons may be blended separately with another diesel source to provide more effective product usage.

In addition, the light diesel hydrocarbons removed in the heavy gasoline splitter may include at least some, and in some examples a majority, of the residual durene that may remain after treatment in the HGT reactor, thereby advantageously decreasing the durene content in the blended final product gasoline as compared to conventional processes. The durene content in the light diesel hydrocarbons may vary based upon the cut points established for the heavy gasoline splitter in particular process configurations. Advantageously, the light diesel hydrocarbons obtained from the disclosed processes may be blended with other diesel sources at a sufficiently low concentration such that the residual durene produces a negligible impact (e.g., lack of crystallization) in the diesel blend. For example, the light diesel hydrocarbons may be blended with other diesel sources such that the durene concentration remains below about 2 wt. %. The light diesel hydrocarbons may also be used for and/or undergo blending with kerosene or an aromatic solvent in other examples. Various implementations of the MTG conversion processes disclosed herein may involve a flow process, such as a steady flow process, or may involve a batch process.

The present disclosure provides MTG conversion processes that may produce gasoline hydrocarbons (e.g. a heavy gasoline or a final product gasoline) having both a decreased boiling endpoint and a reduced durene content as compared to gasoline hydrocarbons obtained from conventional MTG processes. According to the present disclosure, a reduced durene content means achieving, for example, about 2 wt. % or less durene in the final product gasoline obtained from the MTG process or in a final product gasoline that includes gasoline blended from another source. Reducing the durene content in the heavy gasoline hydrocarbons may allow the disclosed processes to achieve ASTM gasoline specifications while using a preferred concentration or a higher-than-conventional concentration of heavy gasoline hydrocarbons in the final product gasoline. An example of a gasoline specification that may be achieved with the present disclosure is ASTM D-4814, "Standard Specification for Automotive Spark-Ignition Engine Fuel." Using a higher concentration of heavy gasoline hydrocarbons in the final product gasoline according to the present disclosure may have various benefits such as, for example, reducing a stockpile of heavy gasoline hydrocarbons that may otherwise result in conventional processes, causing a steady consumption of heavy gasoline hydrocarbons, providing more effective conversion of methanol feedstock into products, and/or increasing the fuel value (energy content per unit volume or per unit mass) of the final product gasoline.

Advantageously, the present disclosure provides MTG conversion processes that may produce gasoline hydrocarbons (e.g., a heavy gasoline or a final product gasoline) having a reduced boiling endpoint as compared to gasoline hydrocarbons obtained from conventional MTG processes. According to various embodiments of the present disclosure, a reduced boiling endpoint means achieving, for example, a boiling endpoint of 205° C. or less in the heavy gasoline hydrocarbons or in the final product gasoline. Reducing the boiling endpoint of the final product gasoline may allow the disclosed processes to achieve gasoline specifications for markets that might otherwise reject the gasoline based on the boiling endpoint value, even if the durene content of the final product gasoline otherwise meets specifications.

All numerical values in the present disclosure, including the claims, are modified by "about" or "approximately" with respect to the indicated value, and take into account experimental error and variations that would be expected by a person having ordinary skill in the art. Unless otherwise indicated, room temperature is about 25° C.

As used in the present disclosure and claims, the singular forms "a," "an," and "the" include plural forms unless the context clearly dictates otherwise. The term "and/or" as used in a phrase such as "A and/or B" herein is intended to include "A and B," "A or B," "A," and "B."

The term "hydrocarbon" refers to a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different numbers of carbon atoms. The hydrocarbons may be substituted or unsubstituted, linear or branched, cyclic or acyclic, and/or aromatic or aliphatic.

The term "light hydrocarbon gas" refers to hydrocarbon compounds that have four carbon atoms or fewer, which are gases at room temperature and atmospheric pressure. As such, light hydrocarbon gas includes compounds such as methane, ethane, propane, butane, 2-methylpropane, cyclopropane, methylcyclopropane, cyclobutane, mixtures thereof and the like. The term "light hydrocarbon gas" may be used synonymously with "liquid petroleum gas hydrocarbons" herein.

The term "gasoline hydrocarbons" refers to hydrocarbon compounds defined by the gasoline specification is ASTM D-4814, "Standard Specification for Automotive Spark-Ignition Engine Fuel." For example, gasoline hydrocarbons may include hydrocarbon compounds having 5 carbon atoms to 12 carbon atoms that have a vapor pressure of 35 kPa to 82.7 kPa (5.0 psi-12 psi) or higher at 37.8° C. (100° F.). Heavy gasoline hydrocarbons having more than 12 carbon atoms may also be present in some cases.

The term "light gasoline hydrocarbons" refers to hydrocarbon compounds having 5 carbon atoms to 9 carbon atoms, and mixtures thereof, including mixtures with $C_{10+}$ hydrocarbon compounds. Thus, "light gasoline hydrocarbons" may include hydrocarbon compounds having 5 carbon atoms to 10 carbon atoms, which following separation according to the present disclosure may contain about 1 wt. % durene or less.

The term "heavy gasoline hydrocarbons" refers to hydrocarbon compounds having 10 carbon atoms or more, and mixtures thereof, including mixtures with $C_{9-}$ hydrocarbon compounds. Thus, "heavy gasoline hydrocarbons" may include hydrocarbon compounds having 9 carbon atoms or more, which following separation according to the present disclosure may contain about 50 wt. % durene or more. Following HGT treatment and separation of "extra heavy hydrocarbons" according to the disclosure herein, the durene content of the heavy hydrocarbons may be decreased. For at least some processes disclosed herein, the boiling endpoint of heavy gasoline hydrocarbons may be less than about 205° C. following HGT treatment and separation of extra heavy hydrocarbons.

The term "light diesel hydrocarbons" refers to a mixture having at least about 90 wt. % hydrocarbon compounds having 10 carbon atoms or more, in which the hydrocarbon compounds have a boiling point from about 205° C. to about 225° C. or from about 200° C. to about 250° C. The light diesel hydrocarbons obtained from the heavy gasoline splitter may include a low sulfur concentration or a high cetane number as compared to another diesel fuel that may be mixed with it, thereby improving the overall characteristics of the diesel blend that is ultimately obtained.

The term "boiling endpoint" refers to the highest temperature needed to fully vaporize all components of a substance. The boiling endpoint may be reported at atmospheric pressure or at a reduced pressure. Boiling endpoints in the present disclosure may be determined by applying ASTM D-86 Standard Test Method for Distillation of Petroleum Products and Liquid Fuels at Atmospheric Pressure.

Processes of the present disclosure may comprise: providing a feed comprising methanol to a dimethyl ether (DME) reactor, converting at least a portion of the feed in the DME reactor under dimethyl ether formation conditions to produce a first product mixture comprising dimethyl ether, transferring the first product mixture to a methanol-to-gasoline (MTG) reactor, converting at least a portion of the first product mixture in the MTG reactor under methanol-to-gasoline conversion conditions to produce a second product mixture comprising light gasoline hydrocarbons and untreated heavy gasoline hydrocarbons, separating the untreated heavy gasoline hydrocarbons from the light gasoline hydrocarbons, transferring the untreated heavy gasoline hydrocarbons to a heavy gasoline treatment (HGT) reactor, catalytically reacting the untreated heavy gasoline hydrocarbons in the HGT reactor to form a third product mixture; and separating a heavy hydrocarbon fraction from the third product mixture. The heavy hydrocarbon fraction comprises heavy gasoline hydrocarbons having a lower boiling endpoint than does the untreated heavy gasoline hydrocarbons.

Suitable conditions for the reactions of the present processes are described next. The catalyst used to form DME in the DME reaction may include gamma-alumina, as an example. Suitable DME formation conditions in the presence of the catalyst may include a temperature of about 325° C. and a pressure of about 27 bar, for example. Other suitable DME formation conditions may include a temperature in a range of about 300-350° C. and a pressure in a range of about 20-35 bar, as examples. These temperatures and pressures may refer to those measured at the inlet of the reactor in which the reaction is conducted. Under these conditions, a DME reactor may produce an equilibrium mixture of dimethyl ether (DME), methanol, and water resulting in a conversion up to about 78 mol. % DME or even higher. In some examples, the conversion rate may be from 75 to 85 mol. % DME.

The catalyst used to form gasoline hydrocarbons in the MTG reactor may be a zeolite catalyst or, more specifically, a crystalline aluminosilicate zeolite, such as ZSM-5, H-ZSM-5, ZSM-11, ZSM-12, ZSM-22, ZSM-23, ZSM-35, ZSM-48, and the like, and combinations thereof, as examples. Suitable MTG formation or conversion conditions in the presence of the catalyst may include a temperature of about 325° C. and a pressure of about 22 bar, for example. Other suitable MTG formation conditions may include a temperature of about 320-330° C. and a pressure of about 19-25 bar or a temperature of about 315-335° C. and a pressure of about 15-30 bar, as examples. Other suitable MTG conversion conditions may include a temperature in the range of 300-350° C. These temperatures and pressures may refer to those measured at the inlet of the reactor in which the reaction is conducted.

A space velocity within the DME reactor may be about 3.0 hf$^{-1}$, referring to the capability to process a feed stream equivalent to three times the reactor volume each hour. The space velocity within the DME reactor may range from about 2.5 hr$^{-1}$ to about 3.5 hf$^{-1}$, or about 2.0 hr$^{-1}$ to about 4.0 hr$^{-1}$, or about 2.0 hr$^{-1}$ to about 4.0 hf$^{-1}$. A space velocity within the MTG reactor may be about 1.6 hf$^{-1}$, may range from about 1.4 hr$^{-1}$ to about 1.8 hf$^{-1}$, or about 1.2 hr$^{-1}$ to about 2.0 hr$^{-1}$.

Suitable conditions and catalysts for the reactions of the MTG processes of the present disclosure are also described in U.S. Pat. No. 9,938,205 and U.S. Patent Application Publications 2016/0178132, 2017/0121615, and 2018/0170823, which are incorporated herein by reference in their entirety.

In the presence of a suitable catalyst or a plurality of catalysts, further processing of the untreated heavy gasoline hydrocarbons may take place in the HGT reactor, wherein a hydrotreating process may take place. Among the reactions that may occur in the HGT reactor include, for example, disproportionation, isomerization, transalkylation, ring saturation, and dealkylation/cracking. Suitable catalysts that may be present in the HGT reactor include, for example, multifunctional metal catalysts, such as a cobalt molybdenum and/or nickel tungsten catalysts, or Honeywell UOP's HC-26 catalyst in a particular example. Such catalysts may be disposed on an acidic or non-acidic support material. Suitable reaction conditions in the HGT reactor may include, for example, a temperature in the range of about 305° C. to about 320° C. and a pressure in the range of about 33 bar to about 40 bar, particularly a temperature of about 312° C. and a pressure of about 36 bar, as an example. For a total pressure of 36 bar, the hydrogen partial pressure in the HGT reactor may be about 27 bar or above. Illustrative HGT reactions and processes are described further in U.S. Patent Application Publications 2015/0175898, 2017/0137720, and 2017/0137342, each of which is incorporated herein by reference in its entirety.

THE FIG. shows a diagram of system 100 demonstrating various operations that may be performed in the course of converting methanol to gasoline according to various embodiments of the present disclosure. Although system 100 is presented such that methanol-to-gasoline conversion is accomplished via a flow process, particularly a steady flow process, it is to be appreciated that the concepts presented herein may also be implemented as a batch process in alternative embodiments. Referring to THE FIGURE, a feed stream (alternately a feed batch) comprising methanol is provided from methanol supply 101 through feed line 102 to DME reactor 104. The feed stream in feed line 102 may also include other substances, such as water. DME reactor 104 operates under dimethyl ether formation conditions, discussed above, and contains a catalyst that catalytically converts the methanol received from feed line 102 into dimethyl ether (DME) via a dehydration reaction to form a product mixture (equilibrium mixture) comprising dimethyl ether (DME), methanol, and water, which exits DME reactor 104 through line 107. After exiting DME reactor 104, the mixture in line 107 passes to MTG reactor 120, which operates under MTG conversion conditions, discussed above, and contains a catalyst, such as ZSM-5, that is capable of converting the DME into gasoline hydrocarbons. Within MTG reactor 120, the DME interacts with the second catalyst to form a second product mixture comprising gasoline hydrocarbons and light hydrocarbon gas, which exits as a stream through line 125. The gasoline hydrocarbons within the second product mixture may comprise both light gasoline hydrocarbons and heavy gasoline hydrocarbons, including extra heavy gasoline hydrocarbons in some instances.

The second product mixture produced in MTG reactor 120 is delivered via line 125 to separation section 140, wherein separation of light hydrocarbon gas from gasoline hydrocarbons takes place. The light hydrocarbon gas exits separation section 140 as an overhead stream through line 143. Separation section 140 further separates the gasoline hydrocarbons from the second product mixture into at least two fractions of gasoline hydrocarbons: a heavier fraction comprising untreated heavy gasoline hydrocarbons, which exit through line 145, and a lighter fraction comprising light gasoline hydrocarbons, which exit through line 147. A splitter present in separation section 140 may facilitate separation of the heavier fraction from the lighter fraction. The heavier fraction exiting through line 145 also includes a major portion of any durene that is present in the second product mixture from line 125. In some examples, the heavier fraction in line 145 may contain at least about 99 wt. % of the total durene present in the second product mixture from line 125. The heavier fraction in line 145 may comprise greater than or equal to 50 wt. % durene. Thus, separation section 140 is operationally configured to discharge separate fractions of light hydrocarbon gas, light gasoline hydrocarbons, and a heavier fraction comprising untreated heavy gasoline hydrocarbons and optionally enhanced levels of durene. Effluent comprising water may exit separation section 140 separately from the lines that are expressly shown. Although not shown, the light hydrocarbon gas may be recycled to an upstream location in the disclosed processes including, but not limited to, MTG reactor 120. Separation section 140 may include a deethanizer and a debutanizer in particular process configurations, wherein the deethanizer and the debutanizer may exist as discrete apparatus components or be integrated into a single apparatus component. Thus, separation section 140 may comprise a single separation unit or multiple separation units for separating the second product mixture into additional fractions for further processing.

Heavy gasoline hydrocarbons and optionally durene in line 145 are delivered to heavy gasoline treatment (HGT) reactor 160. HGT reactor 160 catalytically converts the durene in the heavy gasoline hydrocarbons to form a third product mixture, which is discharged through line 165. HGT reactor 160 includes a catalyst, possibly including a plurality of catalysts effective for isomerizing durene.

The disclosed process configuration may limit the processing load downstream from HGT reactor 160 and provide capital expenditure advantages. It is to be recognized that alternative process configurations may incorporate HGT reactor 160 within separation section 140. In particular, after deethanization and debutanization, the remaining gasoline hydrocarbons may be processed by HGT reactor 160 before being further separated into light gasoline hydrocarbons and heavy gasoline hydrocarbons in lines 147 and 145, respectively. Further alternately, splitting into light gasoline hydrocarbons and heavy gasoline hydrocarbons may take place before processing in HGT reactor 160 occurs.

After being processed in HGT reactor 160, the third product mixture in line 165 is delivered to separation unit 170, which may be called a heavy gasoline splitter or fractionator. Separation unit 170 separates the third product mixture into a lighter fraction, which may also be referred to as an overhead fraction, comprising heavy gasoline hydrocarbons, which are discharged through line 175, and an extra heavy hydrocarbon fraction comprising light diesel hydrocarbons and optionally a majority of the remaining durene, which are collectively discharged through line 177 and may be referred to as a bottoms fraction. The light diesel hydrocarbons in line 177 may include at least some of the durene remaining after treatment of the heavy hydrocarbons in HGT reactor 160. Due to the sequential arrangement of separation unit 140 and separation unit 170, the heavy gasoline hydrocarbons in line 175 have a lower boiling endpoint than do the untreated heavy gasoline hydrocarbons in line 145, which are obtained as a result of removing the light gasoline hydrocarbons. The light diesel hydrocarbons in line 177 may be further combined with another diesel source in some instances. The extra heavy hydrocarbon fraction comprising light diesel hydrocarbons in line 177 has a boiling endpoint that is equal to or about equal to the boiling endpoint of the third product mixture in line 165, which may be equal to or about equal to the boiling endpoint of the untreated heavy gasoline hydrocarbons in line 145, or greater than the boiling endpoint of the untreated heavy gasoline hydrocarbons in line 145 if additional hydrocarbons with a larger number of carbon atoms are produced in HGT reactor 160.

As shown in THE FIGURE, blending unit 180 may be fluidly coupled to line 147 to receive the light gasoline hydrocarbons and to line 175 to receive the heavy gasoline hydrocarbons that are depleted in light diesel hydrocarbons and/or durene. Blending unit 180 is fluidly coupled to product line 185, which may provide the final product gasoline to a desired location. Some embodiments may include additional processing of the final product gasoline.

The light diesel hydrocarbons in line 177 may include hydrocarbons having a boiling endpoint that is higher than is allowable according to a selected specification for a preferred boiling endpoint of the final product gasoline. The boiling endpoint of the selected specification may be stated as an upper temperature limit, which may be about 205° C. or below, as an example. As a consequence of employing separation unit 170, the heavy hydrocarbon fraction in line 175, which is the overhead fraction, may have a boiling endpoint that is sufficiently low to be acceptable according to the selected specification. The light gasoline hydrocarbons in line 147 have a boiling endpoint that is lower than that of the heavy hydrocarbon fraction in line 175, and therefore the light gasoline hydrocarbons in line 147 may fall within the selected specification. Because the product streams in lines 175 and 147 both meet the selected specification, mixtures resulting from a combination therefrom may also have a boiling endpoint that is within the selected specification.

Continuing to reference THE FIGURE, system 100 may include one or more of the following features. Separation unit 170 may be, for example, a distillation column in which line 175 comprises an overhead outlet to discharge the heavy hydrocarbon fraction, and line 177 comprises a bottoms outlet to discharge the light diesel hydrocarbons. Separation unit 170 may alternately be positioned before HGT reactor 160, or another separation unit 170 may be placed before HGT reactor 160, in addition to separation unit 170 currently depicted in THE FIGURE Reactors 104 and 120 may be fixed-bed reactors, according to various embodiments of the present disclosure. In alternative process configurations, at least one of reactors 104 or 120 may be a fluidized bed reactor.

Other configurations for system 100 may be developed based on the present disclosure. System 100 may include additional components to perform such tasks as heating, cooling, additional separation processes, compressing, or flashing, as examples. The additional equipment may be located at any suitable location before, after, or between any of the previously disclosed components. As mentioned above, for example, separation section 140 may comprise a single separation unit or may comprise a plurality of separation units and may separate the second product mixture into additional fractions or streams of fluids. Separation section 140 may include a de-ethanizer to remove ethane from the second product mixture as a separate stream. Separation section 140 may include a stabilizer that is configured to remove liquid petroleum gas hydrocarbons as a separate stream, thereby removing them from the second product mixture and the light hydrocarbon gas in line 143. Separation section 140 may include a splitter configured to provide the heavy gasoline hydrocarbons, including durene when present, and light gasoline hydrocarbons, as described above. Separating the second product mixture using separation section 140 may comprise passing the heavy gasoline hydrocarbons through at least three separation units prior to entering line 145.

Alternately, separation unit 170 may be replaced or supplemented by a separation drum or a stripping section configured to condense or remove light diesel hydrocarbons before further processing the heavy gasoline hydrocarbons. For example, a separation drum or stripping section may be upstream of HGT reactor 160 to promote separation of light diesel hydrocarbons before further processing the heavy gasoline hydrocarbons. Moreover, the second product mixture in line 125 obtained from MTG reactor 120 may pass through a feed/effluent heat exchanger (not shown) to be cooled by an effluent stream of system 100, and the second product mixture may then pass through an additional separation unit (not shown). The additional equipment may generate a stream having a similar composition to that of the stream in line 177. This additional cooling process may be highly selective, condensing substantially the light-diesel components. A separation unit (e.g., a separation drum or flash unit) may be used to separate a condensed portion of the light diesel hydrocarbons from the second product mixture. The temperature to which the second product mixture obtained from MTG reactor 120 is cooled can be controlled in such a way that the condensed portion contains or is nearly limited to substantially light diesel hydrocarbons, when present. The light diesel hydrocarbons may be separated as a liquid and may join with line 177 for further processing. The remaining portion of the second product mixture, which is in vapor phase at this point in the process, is then delivered to separation section 140 for further processing.

Embodiments disclosed herein include:

A. Methods for Methanol-to-Gasoline conversion with a separation operation following heavy gasoline treatment. The methods comprise: providing a feed comprising methanol to a dimethyl ether (DME) reactor; converting at least a portion of the feed in the DME reactor under dimethyl ether formation conditions to produce a first product mixture comprising dimethyl ether; transferring the first product mixture to a methanol-to-gasoline (MTG) reactor; converting at least a portion of the first product mixture in the MTG reactor under methanol-to-gasoline conversion conditions to produce a second product mixture comprising light gasoline hydrocarbons and untreated heavy gasoline hydrocarbons; separating the untreated heavy gasoline hydrocarbons from the light gasoline hydrocarbons; transferring the untreated heavy gasoline hydrocarbons to a heavy gasoline treatment (HGT) reactor; catalytically reacting the untreated heavy gasoline hydrocarbons in the HGT reactor to form a third product mixture; and separating a heavy hydrocarbon fraction from the third product mixture, the heavy hydrocarbon fraction comprising heavy gasoline hydrocarbons having a lower boiling endpoint than does the untreated heavy gasoline hydrocarbons.

The above-disclosed methods may have one or more of the following additional elements in any combination:

Element 1: wherein the method further comprises blending at least a portion of the light gasoline hydrocarbons with at least a portion of the heavy hydrocarbon fraction.

Element 2: wherein the method further comprises separating an extra heavy hydrocarbon fraction from the third product mixture, the extra heavy hydrocarbons comprising light diesel hydrocarbons.

Element 3: wherein the method further comprises blending at least a portion of the extra heavy fraction with a separate diesel source.

Element 4: wherein the extra heavy fraction further comprises durene.

Element 5: wherein the method further comprises separating liquid petroleum gas hydrocarbons from the second product mixture.

Element 6: wherein heavy gasoline hydrocarbons pass through at least three separation units to obtain the heavy hydrocarbon fraction.

Element 7: wherein the HGT reactor contains a plurality of catalysts.

Element 8: wherein separating the heavy hydrocarbon fraction from the third product mixture takes place in a separation unit that is fluidly coupled to receive at least a portion of the third product mixture from the HGT reactor and configured to discharge the heavy hydrocarbon fraction separately from light diesel hydrocarbons; and wherein a blending unit is fluidly coupled to receive at least a portion of the heavy hydrocarbon fraction and blend the heavy hydrocarbon fraction with at least a portion of the light gasoline hydrocarbons.

Element 9: wherein the method further comprises blending at least a portion of the light diesel hydrocarbons with a separate diesel source.

Element 10: wherein the feed is provided to the DME reactor continuously as part of a flow process.

By way of non-limiting example, exemplary combinations applicable to A include: 1 and 2; 1, 2 and 3; 1, 2, and 4; 1, 2, 3, and 4; 1 or 2 and 5; 1 or 2 and 6; 1 or 2 and 7; 1 or 2 and 8; 1 or 2, 8, and 9; 1 or 2 and 10; 2, 3, and 4; 2, 3, and 5; 2, 3, and 6; 2, 3, and 7; 2, 3, and 8; 2, 3, 8, and 9; 2, 3, and 10; 2, 4, and 5; 2, 4, and 6; 2, 4, and 7; 2, 4, and 8; 2, 4, 8, and 9; 2, 4, and 10; 2, 3, 4, and 5; 2, 3, 4, and 6; 2, 3, 4, and 7; 2, 3, 4, and 8; 2, 3, 4, 8, and 9; 2, 3, 4, and 10; 5 and 6; 5 or 6 and 7; 5 or 6 and 8; 5 or 6 8, and 9; 5 or 6 and 10; 7 and 8; 7, 8 and 9; 7 or 8 and 10; and 8, 9, and 10.

Any documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

Unless otherwise indicated, all numbers expressing quantities of ingredients, properties such as molecular weight, process conditions, and so forth used in the present disclosure are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. For the methods herein, the order of various process steps may be rearranged in some embodiments and yet remain within the scope of the disclosure, including the claims.

One or more illustrative embodiments are presented herein. Not all features of a physical implementation are described or shown in this application for the sake of clarity. It is understood that in the development of a physical embodiment of the present disclosure, numerous implementation-specific decisions must be made to achieve the developer's goals, such as compliance with system-related, business-related, government-related, and other constraints, which vary by implementation and from time to time. While a developer's efforts might be time-consuming, such efforts would be, nevertheless, a routine undertaking for one of ordinary skill in the art and having benefit of this disclosure.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein.

The invention claimed is:

1. A method comprising:
   providing a feed comprising methanol to a dimethyl ether (DME) reactor;
   converting at least a portion of the feed in the DME reactor under dimethyl ether formation conditions to produce a first product mixture comprising dimethyl ether;
   transferring the first product mixture to a methanol-to-gasoline (MTG) reactor;
   converting at least a portion of the first product mixture in the MTG reactor under methanol-to-gasoline conversion conditions to produce a second product mixture comprising light gasoline hydrocarbons and untreated heavy gasoline hydrocarbons;
   separating the untreated heavy gasoline hydrocarbons from the light gasoline hydrocarbons, the untreated heavy gasoline hydrocarbons comprising more than 50% by weight of durene;
   transferring the untreated heavy gasoline hydrocarbons to a heavy gasoline treatment (HGT) reactor;
   catalytically reacting the untreated heavy gasoline hydrocarbons in the HGT reactor to form a third product mixture, the catalytically reacting comprising exposing the untreated heavy gasoline hydrocarbons to at least one catalyst in the presence of hydrogen; and
   separating a heavy hydrocarbon fraction from the third product mixture, the heavy hydrocarbon fraction comprising heavy gasoline hydrocarbons having a lower boiling endpoint than do the untreated heavy gasoline hydrocarbons.

2. The method of claim 1, further comprising:
   blending at least a portion of the light gasoline hydrocarbons with at least a portion of the heavy hydrocarbon fraction.

3. The method of claim 1, further comprising:
   separating an extra heavy hydrocarbon fraction from the third product mixture, the extra heavy hydrocarbons comprising light diesel hydrocarbons.

4. The method of claim 3, further comprising:
   blending at least a portion of the extra heavy hydrocarbon fraction with a separate diesel source.

5. The method of claim 3, wherein the extra heavy hydrocarbon fraction further comprises durene.

6. The method of claim 1, further comprising:
   separating liquid petroleum gas hydrocarbons from the second product mixture.

7. The method of claim 1, wherein heavy gasoline hydrocarbons pass through at least three separation units to obtain the heavy hydrocarbon fraction.

8. The method of claim 1, wherein the HGT reactor contains a plurality of catalysts.

9. The method of claim 1, wherein separating the heavy hydrocarbon fraction from the third product mixture takes place in a separation unit that is fluidly coupled to receive at least a portion of the third product mixture from the HGT reactor and configured to discharge the heavy hydrocarbon fraction separately from light diesel hydrocarbons; and wherein a blending unit is fluidly coupled to receive at least a portion of the heavy hydrocarbon fraction and blend the heavy hydrocarbon fraction with at least a portion of the light gasoline hydrocarbons.

10. The method of claim 9, further comprising:
    blending at least a portion of the light diesel hydrocarbons with a separate diesel source.

11. The method of claim 1, wherein the feed is provided to the DME reactor continuously as part of a flow process.

12. The method of claim 1, wherein the third product mixture comprises more than 10% by weight of durene.

* * * * *